US008238591B2

(12) United States Patent
Latzel

(10) Patent No.: US 8,238,591 B2
(45) Date of Patent: Aug. 7, 2012

(54) METHOD FOR DETERMINING A TIME CONSTANT OF THE HEARING AND METHOD FOR ADJUSTING A HEARING APPARATUS

(75) Inventor: Matthias Latzel, Eggolsheim (DE)

(73) Assignee: Siemens Medical Instruments Pte. Ltd., Singapore (SG)

( * ) Notice: Subject to any disclaimer, the term of this patent is extended or adjusted under 35 U.S.C. 154(b) by 528 days.

(21) Appl. No.: 12/384,869

(22) Filed: Apr. 9, 2009

(65) Prior Publication Data

US 2009/0264793 A1    Oct. 22, 2009

(30) Foreign Application Priority Data

Apr. 17, 2008  (DE) .......................... 10 2008 019 374

(51) Int. Cl.
*H04R 25/00* (2006.01)
*A61B 5/00* (2006.01)
(52) U.S. Cl. ..................... 381/312; 381/60; 600/559
(58) Field of Classification Search .............. 600/559; 381/60, 312–331
See application file for complete search history.

(56) References Cited

U.S. PATENT DOCUMENTS

| 6,327,366 | B1* | 12/2001 | Uvacek et al. | 381/60 |
|---|---|---|---|---|
| 7,194,100 | B2* | 3/2007 | Kuhnel et al. | 381/321 |
| 7,333,623 | B2* | 2/2008 | Neumann | 381/312 |
| 8,019,105 | B2* | 9/2011 | Kates | 381/321 |
| 2005/0123145 | A1* | 6/2005 | Kuhnel | 381/60 |
| 2005/0175198 | A1* | 8/2005 | Neumann | 381/312 |

FOREIGN PATENT DOCUMENTS

| DE | 2951856 C2 | 7/1981 |
|---|---|---|
| DE | 19703228 A1 | 7/1998 |
| EP | 1290914 B1 | 5/2004 |

* cited by examiner

*Primary Examiner* — Max Hindenburg
*Assistant Examiner* — John Pani

(57) ABSTRACT

A method for adjusting a signal processing facility of a hearing apparatus is provided. An acoustic signal is presented and processing using a signal-processing facility, which has a first-time value to form a first-processed-acoustic signal. The first-processed-acoustic signal is assigned to a first loudness via the user. A renewed presentation of the acoustic signal is processed by the signal-processing facility, which has a second-time value to form a second-processed-acoustic signal as well as an assignment of the second-processed-acoustic signal to form a second loudness by the user. In one aspect the second-time value is less than the first-time value and the steps are repeated until the second loudness equates to the first loudness, with the first-time value being shortened with each repetition. In another aspect the second-time value is greater than the first-time value and the steps are repeated until the second loudness differs from the first loudness, with the first-time value being lengthen with each repetition.

16 Claims, 3 Drawing Sheets

FIG. 1
(Prior art)
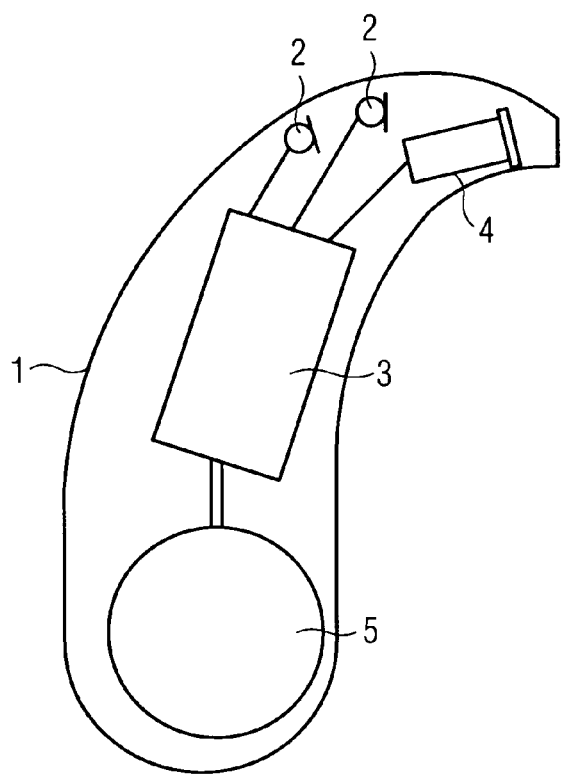
FIG 2
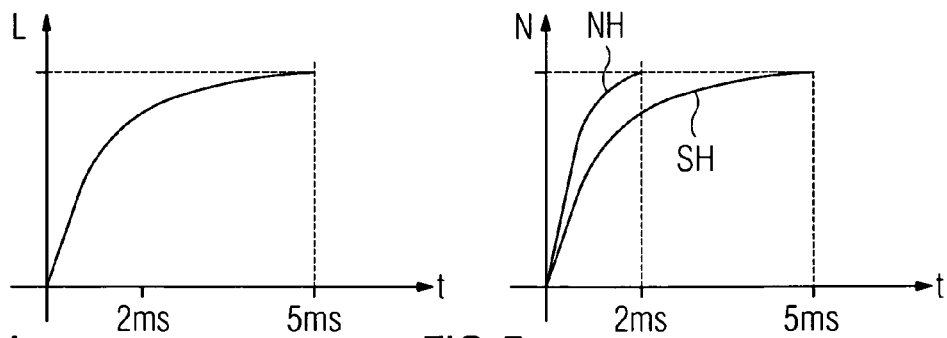
FIG 3
FIG 4
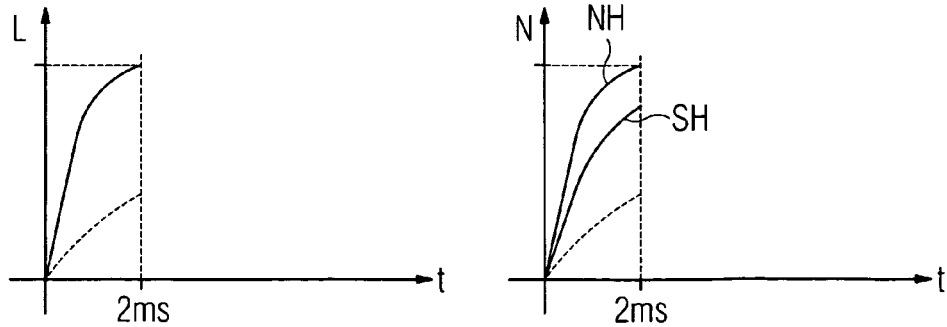
FIG 5

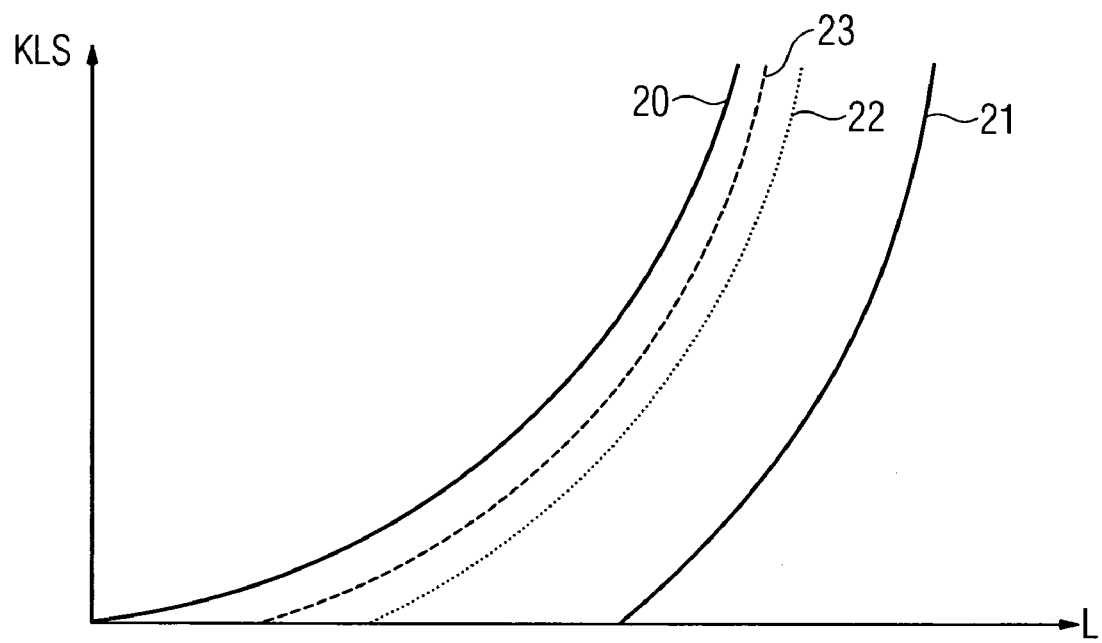

METHOD FOR DETERMINING A TIME CONSTANT OF THE HEARING AND METHOD FOR ADJUSTING A HEARING APPARATUS

CROSS REFERENCE TO RELATED APPLICATIONS

This application claims priority of German application No. 10 2008 019 374.7 DE filed Apr. 17, 2008, which is incorporated by reference herein in its entirety.

FIELD OF INVENTION

The present invention relates to a method for determining a time constant of the hearing of a user. The present invention further relates to a method for adjusting a signal processing algorithm of a hearing apparatus. The term "hearing apparatus" is understood here to mean any device which can be worn in or on the ear, in particular a hearing device, a headset, earphones and such like.

BACKGROUND OF INVENTION

Hearing devices are wearable hearing apparatuses which are used to assist the hard-of-hearing. In order to accommodate numerous individual requirements, various types of hearing devices are available such as behind-the-ear (BTE) hearing devices, hearing device with external receiver (RIC: receiver in the canal) and in-the-ear (ITE) hearing devices, for example also concha hearing devices or completely-in-the-canal (ITE, CIC) hearing devices. The hearing devices listed as examples are worn on the outer ear or in the auditory canal. Bone conduction hearing aids, implantable or vibrotactile hearing aids are also available on the market. The damaged hearing is thus stimulated either mechanically or electrically.

The key components of hearing devices are principally an input converter, an amplifier and an output converter. The input converter is normally a receiving transducer e.g. a microphone and/or an electromagnetic receiver, e.g. an induction coil. The output converter is most frequently realized as an electroacoustic converter e.g. a miniature loudspeaker, or as an electromechanical converter e.g. a bone conduction hearing aid. The amplifier is usually integrated into a signal processing unit. This basic configuration is illustrated in FIG. 1 using the example of a behind-the-ear hearing device. One or a plurality of microphones 2 for recording ambient sound are built into a hearing device housing 1 to be worn behind the ear. A signal processing unit 3 which is also integrated into the hearing device housing 1 processes and amplifies the microphone signals. The output signal for the signal processing unit 3 is transmitted to a loudspeaker or receiver 4, which outputs an acoustic signal. Sound is transmitted through a sound tube, which is affixed in the auditory canal by means of an otoplastic, to the device wearer's eardrum. Power for the hearing device and in particular for the signal processing unit 3 is supplied by means of a battery 5 which is also integrated in the hearing device housing 1.

SUMMARY OF INVENTION

The effective time constants of signal processing facilities and in particular of compression circuits in hearing devices are currently determined in a purely technical sense. In return, there are a series of standards in which the measuring specifications are defined precisely. In the case of purely technical measurements, a value is determined which only has a theoretical reference but does not provide any indication of the efficiency in the case of individual hearing-impaired persons. As these measurements are not perceptive, it is not possible to determine thereby which time constant can still be processed by the hearing-impaired person. The only current method which is used to evaluate the efficiency of the time constants of compression circuits is the use of questionnaires. Here the efficiency of time constants can however only be queried indirectly. This method is also hampered by the known inaccuracy of questionnaires.

As is known, the categorical loudness scaling CLS, which illustrates an assignment of a perception variable (e.g. loud, average, quiet) to a physical variable (e.g. acoustic pressure level) can be used to measure the loudness sensation of the pathological hearing or to determine the efficiency of the hearing devices. Suitable narrow band signals are chosen here on the one hand in order to achieve frequency-specific data and adequately long signals are chosen on the other hand in order to determine the efficiency of the hearing device in the engaged state. For instance, the reaction of interference noise suppression algorithms can be awaited with adequately long signals.

The object of the present invention thus consists in specifying a method, with which the time constant of the hearing of a user can be determined with increased accuracy. Furthermore, a method is to be specified, with which the signal processing facility of a hearing apparatus can be better adjusted in respect of a reduced energy consumption.

In accordance with the invention, this object is achieved by a method for determining a time constant of the hearing of a user comprising the steps: presenting an acoustic signal, processing the acoustic signal using a signal processing facility, which has a first time constant, to form a processed first acoustic signal, assigning the first acoustic signal to form a first loudness by means of the user, re-presenting the acoustic signal, processing the acoustic signal using the signal processing facility, the time constant of which is reduced to a shorter second time constant compared with the first time constant, to form a processed second acoustic signal, assigning the second acoustic signal to a second loudness by means of the user, repeating the processed steps until the second loudness equates to the first loudness, with a first time constant being shortened with each repetition and defining the resulting first or second time constant as the time constant of the hearing of the user.

It is thus advantageously possible to determine the time resolution of the hearing on the basis of the loudness sensation of the individual hearing.

Provision is further made in accordance with the invention for a method for adjusting a signal processing facility in a hearing apparatus comprising the steps: presenting an acoustic signal, processing the acoustic signal using the signal processing facility, which has a first time constant, to form a processed first acoustic signal, assigning the first acoustic signal to form a first loudness by means of the user, re-presenting the acoustic signal, processing the acoustic signal using the signal processing facility, the time constant of which is reduced to a shorter second time constant compared with the first time constant, to form a processed second acoustic signal, assigning the second acoustic signal to a second loudness by means of the user, repeating the preceding steps until the second loudness firstly equates to the first loudness, with the first time constant being shortened with each repetition and adjusting the signal processing facility using the resulting first or second time constant. It is hereby possible to adjust a hearing apparatus and in particular a hearing device exactly to the temporal hearing ability of a user. In particular, it is hereby possible to prevent the hearing apparatus from having a more minimal time resolution than the user is actually able to perceive. The operation rate and therefore also the energy consumption can also reduce in this way without quality losses.

With the afore-described methods, the first and second loudness are preferably elements of a categorical loudness scaling. This means that the user only has to decide between the values "loud", "average" and "quiet" for instance when evaluating the loudness.

The signal duration of the acoustic signal is expediently less than or equal to 5 ms and/or 15 ms. With short periods of this type, the time constants of the systems clearly have an influence on the loudness. In practice, a sequence of pulses of this type can naturally be presented with the same acoustic pressure levels in order to facilitate the user in his/her assignment to a corresponding loudness.

The processing of the acoustic signal can comprise an automatic amplifier control. Amplifier controls (AGC; Automatic Game Control) of this type have time constants which are relevant to the respective hearing apparatus and which can be used to optimize said control as far as possible. Such a time constant is mostly also determined by any dynamic compression.

The afore-cited methods can also be implemented for several levels of the acoustic signal. Level loudness curves can thus be recorded and used for an optimization. The sought time constant is then in some instances a compromise between and/or an average value of several time constants. In the present application, the term "loudness" is however also to be understood as a loudness function above the level. In this case, the sought time constant can then be found such that the time constant of the hearing apparatus is reduced until the level loudness function no longer changes at least in regions.

The acoustic signal may also comprise several individual signals with different levels, with the assigned loudnesses being level loudness functions. The sought time constant can thus be determined and/or adjusted on the basis of at least one sub area of level loudness functions.

The afore-cited method for determining or adjusting time constants can also alternatively be realized such that the time constants are increased step by step. The second time constant is then not shorter but instead longer than the first time constant and the repetition takes place so often, not until the two loudnesses are the same but instead until the second loudness differs from the first loudness, with the first time constant during each repetition now not being shortened but instead being lengthened.

BRIEF DESCRIPTION OF THE DRAWINGS

The present invention is described in more detail with reference to the appended drawings, in which;

FIG. 1 shows the basic design of a hearing device according to the prior art;

FIG. 2 shows a time diagram of the volume level of an acoustic pulse;

FIG. 3 shows a time diagram of the loudness sensations of a normal person and a hearing-impaired person.

FIG. 4 shows a time diagram of the volume level of an acoustic pulse which is shortened compared with that of FIG. 2, which is generated with shortened time constants;

FIG. 5 shows a time diagram of the loudness sensations of a normal and a hearing-impaired person in respect of the acoustic pulse in FIG. 4;

FIG. 6 shows a flow chart to determine a time constant and/or to adjust a hearing apparatus and FIG. 7 shows a level loudness diagram to illustrate the influence of the time constant of a signal processing.

DETAILED DESCRIPTION OF INVENTION

Figure 6:
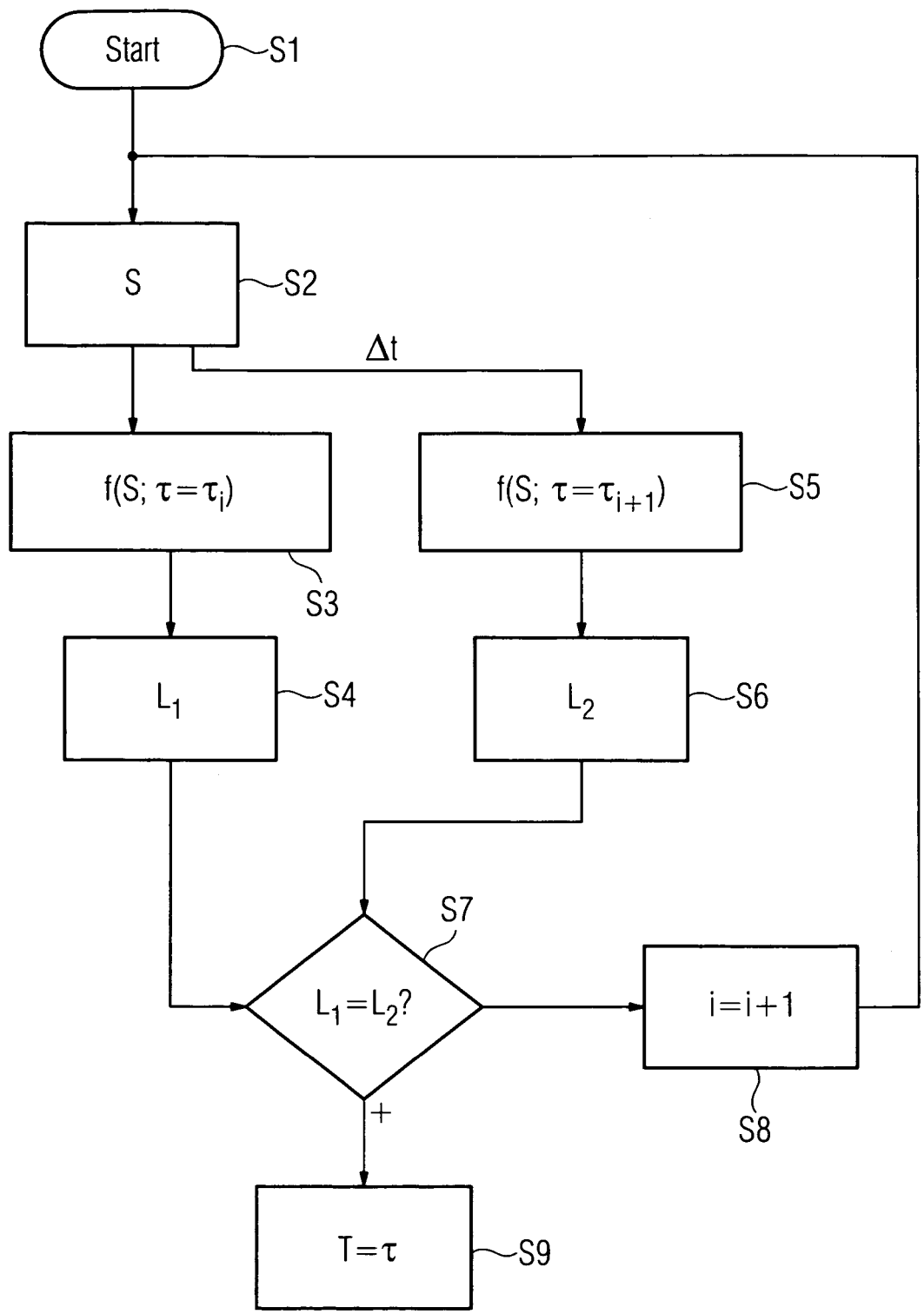

The exemplary embodiments shown in more detail below represent preferred embodiments of the present invention.

It is known that the time resolution ability is negatively affected in the pathological hearing. A suitable signal processing of a hearing device may (partially) compensate for a loss of time resolution abilities. To this end, it may be necessary to determine the effective time constant of the hearing of a user and/or hearing device wearer and/or to adjust the time constant of the signal processing of the hearing device in a suitable fashion.

The significance of the time constants of the hearing and of the signal processing is now explained in a hearing device, in particular the AGC, on the basis of FIG. 2 to 5. A test acoustic pulse is generated in accordance with FIG. 2 for instance, said test acoustic pulse achieving its target acoustic pressure level after approximately 5 ms on the basis of the processing and/or device-specific time constant.

FIG. 3 shows a curve NH, which highlights the time constant of a hearing of a person with normal hearing. The perceived loudness N undergoes practically no further change approximately 2 ms after an erratic increase in the physical acoustic pressure level. By contrast, the curve SH indicates that the integration ability of the hearing of a hearing-impaired person is reduced and a saturation value is only achieved after 5 ms for instance. Accordingly, after the start of the level jump, the hearing-impaired person 2 is still not able to perceive the same loudness as the person with normal hearing. Both nevertheless perceive the same loudness after 5 ms.

FIG. 4 now reproduces a test sound, which was generated by a device and/or a processing unit with a time constant which is reduced compared to FIG. 2. The target acoustic pressure level is already achieved here after 2 ms.

FIG. 5 shows that a person with normal hearing (curve NH) perceives the short test sound in FIG. 4 to be significantly louder than the hearing-impaired person (curve SH). This means that the same test sound is perceived more quietly with a reduced integration ability of the hearing. The hearing-impaired person may thus only profit from a minimal time constant of the signal processing, provided this is longer than the time constant of his/her hearing.

In accordance with the invention, the time constant of the signal processing is now to be adjusted to the time resolution ability of the hearing of the hearing device wearer with the aid of the loudness sensation. This may take place such that the maximum steepness of curve SH is determined on the basis of a variation in the steepness of the curves in FIG. 2 and FIG. 4.

In one exemplary embodiment, the CLS is now used to examine the efficiency of time constants or generally to determine the time processing of the pathological hearing. Special, short signals (with transients) are presented to the hearing device wearer, e.g. a series of drumbeats. These very short signals excite the compression in the hearing device accordingly, depending on the adjusted time constants. The test person, in other words the hearing device wearer, senses a certain loudness of the CLS as a function of the adjusted time constant. It is finally possible to read from the result, i.e. the sensed loudness of the test person, whether the time constant is set (subjectively) correctly.

FIG. 6 shows a flow chart in respect of the method according to the invention. After the start S1 of the method, the test person is presented with a test sound s in step S2. The hearing device processes the short acoustic signal s using its signal processing facility, which has a time constant $\tau_i$ (cf. step S3). The test person perceives the processed acoustic signal according to the categorical loudness $L_1$ (step S4). The time constant of the signal processing facility of the hearing device is now shortened. It now amounts to $\tau_{i+1}$. The test signal s is thereupon presented to the test person again, as shown in FIG. 6 by a At according to step S2. In accordance with step S5, the signal processing now takes place with the shortened time constant $\tau_{i+1}$. The test person perceives the resulting acoustic signal in accordance with the loudness $L_2$ (step S6).

A comparison is carried out in step S7 to determine whether the two loudnesses $L_1$ and $L_2$ are identical. If this is not the case, the loudness proceeds according to the simplified example in FIG. 5 in accordance with the dashed curve. The steps S2 to S7 are therefore repeated with shortened time constants respectively, which is indicated in FIG. 6 with the iteration step i=i+1 (step S8). This means that with another run, the time constant both in step S3 and also in step S5 is shortened in relation to the preceding run.

If the test person finally perceives the two presented sounds as equally loud, i.e. $L_1=L_2$, the time constant thus corresponds to the signal processing facility of that of the hearing of the hearing-impaired person or lies marginally thereabove (within the step size). The time constant does not need to be shortened further. Further computing operations, which were necessary for an additional shortening of the time constant, must therefore not be implemented in the hearing device, as a result of which processing time and energy can be saved.

Varying the time constant of the compression and/or the signal processing also allows the minimal time resolution ability of the hearing-impaired person to be determined. To this end, as described for the adjustment of the hearing device, the time constant is reduced until the loudness no longer changes. In this case, the processing time of the hearing device is then too short and can no longer be resolved from the pathological hearing. The determined time constant $\tau$ can then be evaluated as the time constant of the hearing (step S9).

One further embodiment of the present invention is shown in FIG. 7. A level loudness function, here a CLS target function 20 of a person with normal hearing, is shown there by way of the level L for a certain signal. The pathological level loudness function 21 of the hearing-impaired person is also indicated for the same signal. A level loudness function 22 can now be achieved with a hearing device with a lower time resolution. If the time constant of the hearing device is shortened, the loudness perception is changed such that a level loudness function results according to curve 23. The minimum of the time resolution is then achieved if the position and steepness of the level loudness function can no longer be changed by reducing the time constant.

In order to find the sought time constants, a signal processing facility with a very short time constant can be used as the starting point. The time constant is then enlarged successively. Provided the time resolution of the signal processing is significantly shorter than that of the hearing of the hearing device wearer, the hearing device wearer will then not perceive any loudness difference. It is only if the time resolution of the signal processing is less than that of the hearing that the loudness reduction is adjusted. This threshold is then characterized in turn by the sought time constant.

The afore-illustrated method according to the invention allows on the one hand the minimal time constant to be determined in the compression circuits, which can still be triggered by an individual, pathological hearing. On the other hand, these methods can also be used to adjust the time constant to the individual requirements of the hearing device wearer, by predetermining a CLS as a target function (person with normal hearing CLS) and (interactively) varying the time constant in the compression circuit until the target function is reached by the hearing-impaired persons with a hearing device.

The invention claimed is:

1. A method for determining a time constant of a hearing of a user comprising the steps:
   a) receiving a first acoustic test signal with a hearing aid of a user;
   b) processing the received first acoustic test signal using a signal processing unit of the hearing aid, the signal processing unit having an adjustable time constant that affects a time to reach a target acoustic pressure level, wherein the signal processing unit uses a first time constant to form a first processed acoustic signal output to the user;
   c) assigning the first processed acoustic signal to a first loudness level as perceived by the user,
   d) receiving a second acoustic test signal equivalent to the first acoustic test signal with the hearing aid of the user;
   e) processing the received second acoustic test signal using the signal processing unit of the hearing aid, wherein the signal processing unit uses a second time constant which is shorter than the first time constant to form a second processed acoustic signal output to the user;
   f) assigning the second processed acoustic signal to a second loudness level as perceived by the user, and
   g) comparing the first loudness level to the second loudness level, wherein:
   when the compared first loudness level does not equal the compared second loudness level, the method further comprises the steps of:
   reducing the first time constant; and
   repeating steps a through g, and
   when the compared first loudness level equals the compared second loudness level, the method further comprises the steps of:
   defining the first time constant or the second time constant as the time constant of the hearing of the user, the time constant representing a time resolution ability of the hearing of the user based on the user's loudness perception.

2. The method as claimed in claim 1, wherein the first and second loudness levels are elements of a categorical loudness scaling.

3. The method as claimed in claim 1, wherein a duration of the acoustic test signals is less than or equal to 15 ms.

4. The method as claimed in claim 1, wherein the processing of the acoustic test signals comprises processing with automatic amplifier control.

5. The method as claimed in claim 1, wherein the processing of the acoustic signals comprises processing with dynamic compression.

6. The method as claimed in claim 1, wherein the steps a through g are repeated with a different level of the acoustic test signals.

7. The method as claimed in claim 1, wherein each of the acoustic test signals includes a plurality of individual signals each having a different level.

8. The method as claimed in claim 7, wherein the assigned loudness levels are level loudness functions.

9. A method for determining a time constant of a hearing of a user comprising the steps:
   a) receiving a first acoustic test signal with a hearing aid of a user;

b) processing the received first acoustic test signal using a signal processing unit of the hearing aid, the signal processing unit having an adjustable time constant that affects a time to reach a target acoustic pressure level, wherein the signal processing unit uses a first time constant, to form a first processed acoustic signal output to the user;

c) assigning the first processed acoustic signal to a first loudness level as perceived by the user, d) receiving second acoustic test signal equivalent to the first acoustic test signal with the hearing aid of the user;

e) processing the received second acoustic test signal using the signal processing unit, wherein the signal processing unit uses a second time constant which is shorter than the first time constant, to form a second processed acoustic signal output to the user;

f) assigning the second processed acoustic signal to a second loudness level as perceived by the user, and g) comparing the first loudness level to the second loudness level, wherein:

when the compared first loudness level does not equal the compared second loudness level, the method further comprises the steps of:
   reducing the first time constant; and
   repeating steps a through g, and when the compared first loudness level equals the compared second loudness level, the method further comprises the steps of:
   adjusting the adjustable time constant of the signal processing facility to match the first or second time constant.

10. The method as claimed in claim 9, wherein the first and second loudness levels are elements of a categorical loudness scaling.

11. The method as claimed in claim 9, wherein a duration of the acoustic test signals is less than or equal to 15 ms.

12. The method as claimed in claim 9, wherein the processing of the acoustic test signals includes an automatic amplifier control.

13. The method as claimed in claim 9, wherein the processing of the acoustic test signals includes a dynamics compression.

14. The method as claimed in claim 9, wherein the steps a through g are repeated with a different level of the acoustic test signals.

15. The method as claimed in claim 9, wherein each of the acoustic test signals includes a plurality of individual signals each having a different level.

16. The method as claimed in claim 15, wherein the assigned loudness levels are level loudness functions.

* * * * *